US006450955B1

(12) United States Patent
Brown et al.

(10) Patent No.: US 6,450,955 B1
(45) Date of Patent: *Sep. 17, 2002

(54) MONITORING USER HEALTH AS MEASURED BY MULTIPLE DIVERSE HEALTH MEASUREMENT DEVICES AT A PORTABLE COMPUTER SYSTEM

(75) Inventors: Michael Wayne Brown, Georgetown; Kelvin Roderick Lawrence; Michael A. Paolini, both of Round Rock, all of TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/560,374

(22) Filed: Apr. 28, 2000

(51) Int. Cl.$^7$ .................................................. A61B 5/00
(52) U.S. Cl. ...................................................... 600/300
(58) Field of Search ................................ 600/300, 301, 600/302, 303, 304, 305

(56) References Cited

U.S. PATENT DOCUMENTS

| | | | |
|---|---|---|---|
| 5,410,471 A | | 4/1995 | Alyfuku et al. |
| 5,720,619 A | | 2/1998 | Fisslinger |
| 5,823,948 A | * | 10/1998 | Ross, Jr. et al. ............ 600/300 |
| 6,234,963 B1 | * | 5/2001 | Blike et al. .................. 600/300 |
| 6,248,067 B1 | * | 6/2001 | Causey, III et al. ......... 600/365 |

OTHER PUBLICATIONS

Johnson & Johnson Lifescan, Jan. 17, 2000 "In Touch Diabetes Management Software".
The Wall Street Journal, Thomas E. Weber, Jan. 17, 2000 A Doctor, 700 Patients And The Net: Inventing The Virtual House Call.

* cited by examiner

Primary Examiner—Kevin Shaver
Assistant Examiner—Pamela Wingood
(74) Attorney, Agent, or Firm—Marilyn Smith Dawkins; Bracewell & Patterson, L.L.P.

(57) ABSTRACT

According to the present invention, physical health indicators computed for a particular user are received in a common transmittable data format at a portable computer system associated with the particular user, wherein each of the physical health indicators is computed by an electronic health measurement device from among multiple diverse electronic health measurement devices monitoring the physical health of the particular user. Each of the physical health indicators is analyzed at the portable computer system in view of determined acceptable health levels for the particular user. Output of an indicator of acceptability of the physical health indicators for the particular user is controlled from the portable computer system, in response to the analysis of each of the physical health indicators, such that a single portable computer system monitors the physical health of an individual from multiple physical health indicators received from multiple diverse electronic health measurement devices.

33 Claims, 8 Drawing Sheets

Fig. 4

| Health Indicator measurement {72} | Date/Time {74} | Measurement unit {76} |
|---|---|---|
| 60 | 11/12/2000/06:10:20 | Beats/minute |
| ••• | ••• | ••• |
| 80 | 11/13/2000/07:15:12 | Beats/minute |

| Type of measurement to take {82} | Date/Time {84} | Range {86} |
|---|---|---|
| ••• | ••• | ••• |
| Blood pressure | 11/18/2000/10:00:00 | 01:00:00 |
| Heart Rate | 11/18/2000/11:00:00 | 00:30:00 |
| Blood pressure | 11/18/2000/16:00:00 | 01:00:00 |
| ••• | ••• | ••• |

{88}

| UserID | Password | Birth date | ... | Output preference |
|--------|----------|------------|-----|-------------------|
| GeorgeG | 45ghr5 | 10/20/45 | ... | Colorblind ready |
| SylviaS | Cats20 | 6/6/48 | ... | Large font |
| ... | ... | ... | ... | ... |

*Fig. 6*

MONITORING USER HEALTH AS MEASURED BY MULTIPLE DIVERSE HEALTH MEASUREMENT DEVICES AT A PORTABLE COMPUTER SYSTEM

BACKGROUND OF THE INVENTION

1. Technical Field

The present invention relates in general to a health monitoring device and in particular to a method, system and program for monitoring the outputs of multiple diverse health measurement devices. Still more particularly, the present invention relates to a method, system and program for utilizing a single data processing system to monitor the physical health of a user from health indicators received from multiple diverse health measurement devices.

2. Description of the Related Art

Conventional electronic health measurement devices provide for taking measurements that are computed to reflect the physical health of an individual. In particular, an electronic health measurement device is able to translate a measurement, such as weight on a scale, into a numerical output. For example, diabetics utilize electronic testers that monitor blood or other secretions to determine a number associated with the individual's current glucose levels. In another example, an electronic pulse detector may be placed on an individual's body or gripped by the individual in order to detect the user's current pulse level and compute a representation of the pulse level. In these examples, the computed numbers are associated with a scale of measurement that has been assigned to that type of physical health measurement. An individual may be able to consult a chart or other documentation to discern the meaning of the computed number. For example, a computed weight may be compared with a chart containing preferable weights for an individual of a particular height and age. A computed pulse level may be compared with a chart showing acceptable pulse levels during exercise depending upon age.

While conventional electronic health measurement devices provide a computed number that can be utilized by an individual to monitor that portion of their physical health, there is a need for electronically documenting the measured data in a timely manner. In addition, while some electronic health measurement devices do provide for electronically documenting the measured data, there is a need to electronically document output data from multiple diverse electronic health measurement devices at a single device such that a comprehensive physical health profile can be determined. Moreover, while an individual may be able to consult a chart or other textual data to discern the meaning of a number computed by an electronic health measurement device, this data is not always available, may not be current, may not provide recommendations for how to respond to particular measurement values, and may not provide analysis of measurements from multiple diverse electronic health measurement devices. In view of the foregoing, it is desirable that a method, system and program be provided for monitoring multiple diverse electronic health measurement devices at a single personal data processing system in order to store monitored health related data over a period of time and in order to assist the user by analyzing the monitored measurements and recommending actions.

SUMMARY OF THE INVENTION

In view of the foregoing, it is therefore an object of the present invention to provide an improved health measurement monitoring device.

It is another object of the present invention to provide an improved method, system and program for monitoring the output of multiple diverse health measurement devices.

It is yet another object of the present invention to provide an improved method, system and program for utilizing a single data processing system to monitor the physical health of a user from health indicators received from multiple diverse health measurement devices.

According to the present invention, physical health indicators computed for a particular user are received in a common transmittable data format at a portable computer system associated with the particular user, wherein each of the physical health indicators is output by an electronic health measurement device from among multiple diverse electronic health measurement devices monitoring the physical health of the particular user. Each of the physical health indicators is analyzed at the portable computer system in view of determined acceptable health levels for the particular user. Output of an indicator of acceptability of the physical health indicators for the particular user is controlled from the portable computer system, in response to the analysis of each of the physical health indicators, such that a single portable computer system may be utilized to monitor the physical health of an individual from multiple physical health indicators received from multiple diverse electronic health measurement devices.

All objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

FIG. 4 depicts one embodiment of a block diagram of a data storage structure for the health indicator storage in accordance with the method, system and program of the present invention;

FIG. 5 illustrates one embodiment of a block diagram of a data storage structure for the measurement scheduler in accordance with the method, system and program of the present invention;

FIG. 6 depicts one embodiment of a block diagram of a data storage structure for health profiles in accordance with the method, system and program of the present embodiment;

DETAILED DESCRIPTION OF ILLUSTRATIVE EMBODIMENT

The present invention may be executed in a variety of systems, including a variety of computing systems and electronic devices under a number of different operating systems. In a preferred embodiment of the present invention, the computer system is a portable computing system such as a notebook computer, a palmtop computer, a personal digital assistant, a telephone or other electronic computing system that may also incorporate communications features that provides for telephony, enhanced telephony, messaging and information services. However, the computer system may also be, for example, a desktop computer, a network computer, a midrange computer or a mainframe computer. Preferably, in order to enable at least one of these communications features, the computer system is able to be connected to a network, such as the Internet by either a wired link or wireless link. In addition, the computer system may be a stand-alone system or part of a network such as a local-area network (LAN) or a wide-area network (WAN). Therefore, in general, the present invention is preferably executed in a computer system that performs computing tasks such as manipulating data in storage that is accessible to the computer system. In addition, the computer system includes at least one output device and at least one input device.

Figure 1:
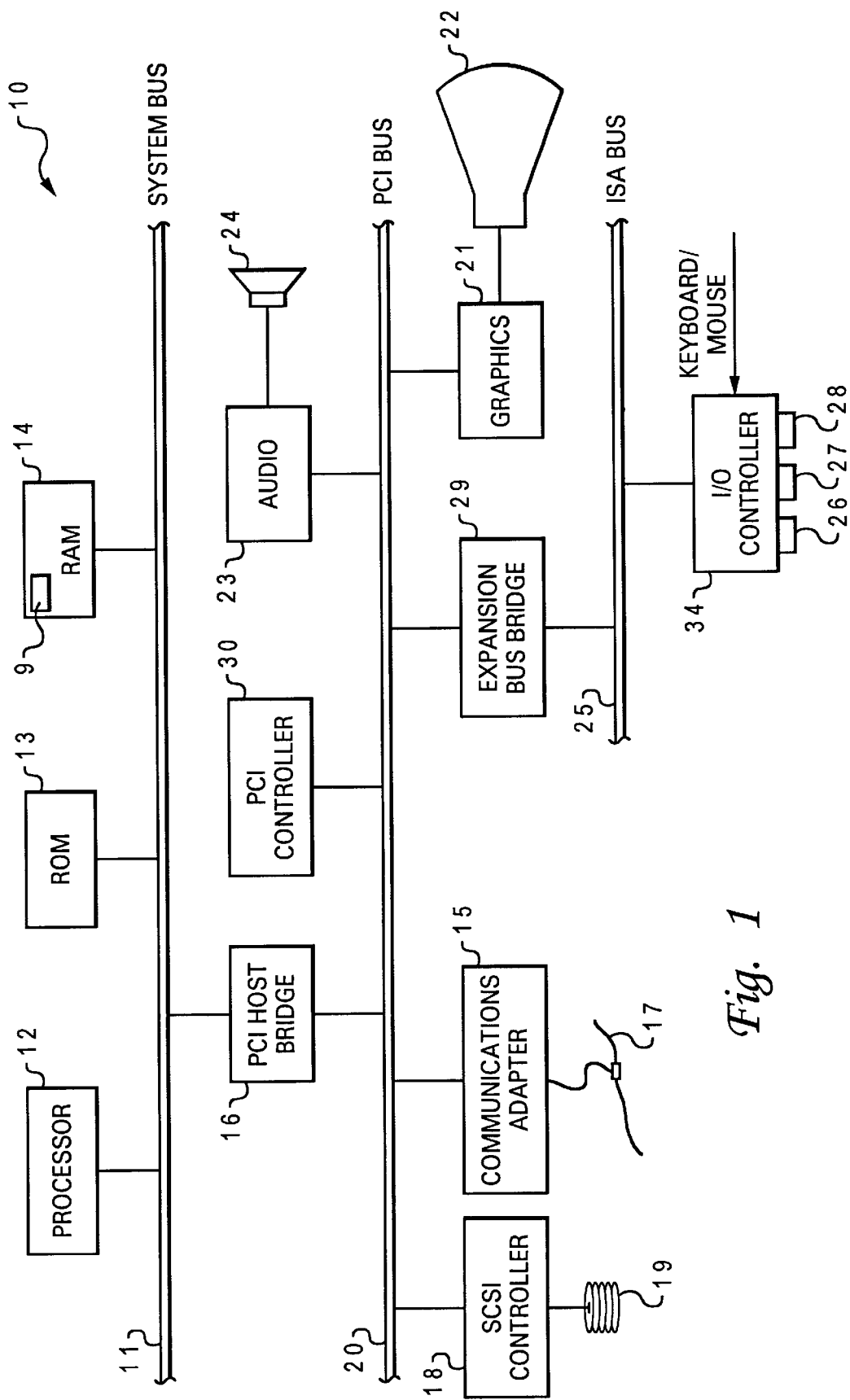
FIG. 1 depicts one embodiment of a data processing system with which the method, system and program of the present invention may advantageously be utilized.

Referring now to the drawings and in particular to FIG. 1, there is depicted a block diagram of one embodiment of a computer system that may utilize the present invention. As depicted, data processing system 10 includes at least one processor 12, which is coupled to system bus 11. Each processor 12 is a general-purpose processor, such as IBM's PowerPC™ processor that, during normal operation, processes data under the control of operating system and application software stored in random access memory (RAM) 14 and Read Only Memory (ROM) 13. The operating system preferably provides a graphical user interface (GUI) to the user. Application software contains instructions that when executed on processor 12 carry out the operations depicted in the flowcharts of FIGS. 7, 8, 9 and others described herein.

Processors 12 are coupled via system bus 11 and Peripheral Component Interconnect (PCI) host bridge 16 to PCI local bus 20. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

PCI local bus 20 interconnects a number of devices for communication under the control of PCI controller 30. These devices include a Small Computer System Interface (SCSI) controller 18, which provides an interface to SCSI hard disk 19, and communications adapter(s) 15, which interface data processing system 10 to at least one data communication network 17 comprising wired and/or wireless network communications. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

PCI local bus 20 is further coupled to an Industry Standard Architecture (ISA) bus 25 by an expansion bus bridge 29. As shown, ISA bus 25 has an attached I/O (Input/Output) controller 34 that interfaces data processing system 10 to peripheral input devices such as a keyboard and mouse (not illustrated) and supports external communication via parallel, serial and universal serial bus (USB) ports 26, 27, and 28, respectively.

Figure 2:
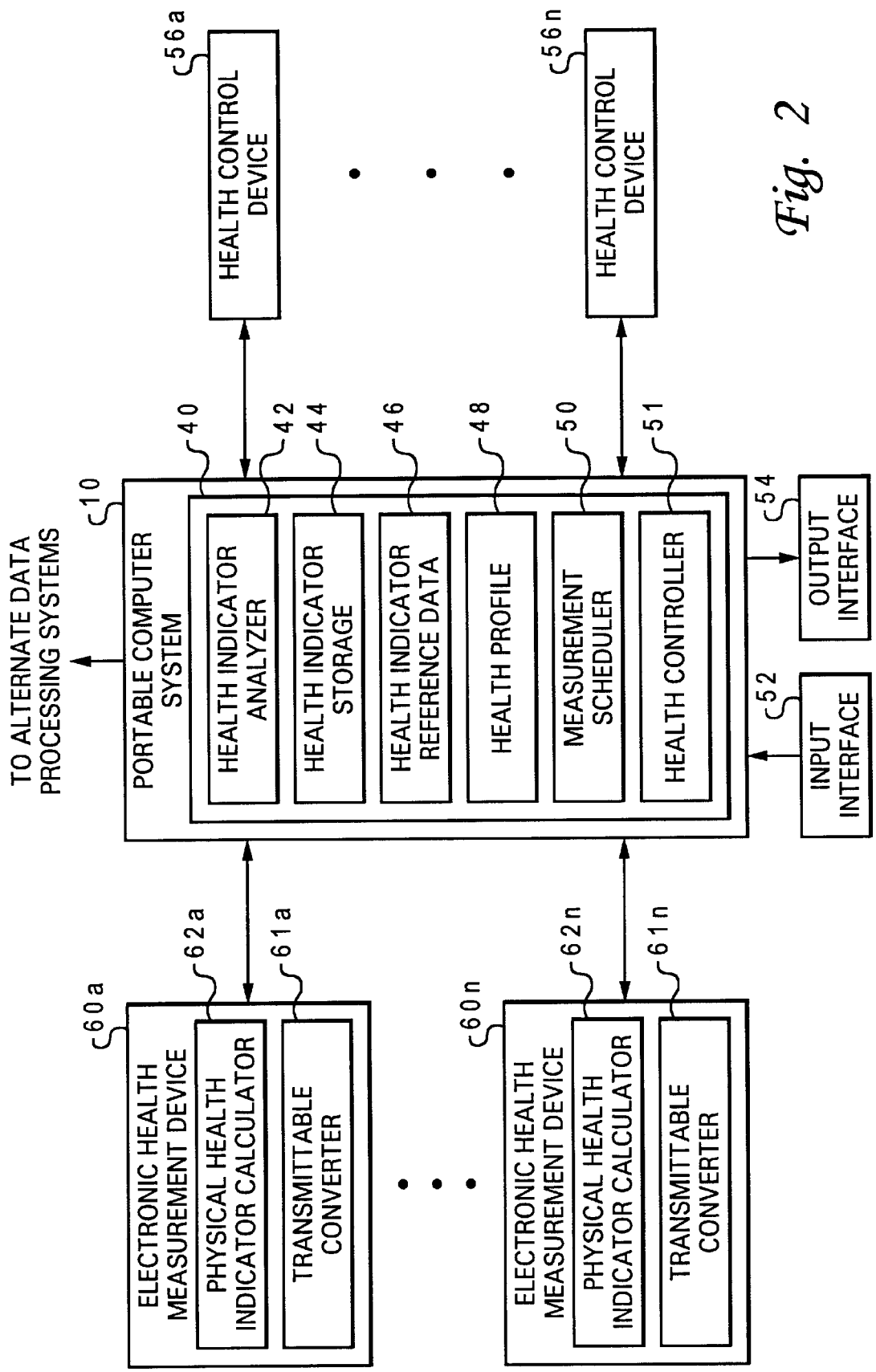
FIG. 2 illustrates one embodiment of a block diagram of an electronic health measurement device monitoring system in accordance with the method, system and program of the present invention.

With reference now to FIG. 2, there is illustrated a block diagram of an electronic health measurement device monitoring system in accordance with the method, system and program of the present invention. As depicted, a computer system 10 communicates with multiple diverse electronic health measurement devices 60a–60n via a communications medium (or across a communication interface). In addition, computer system 10 communicates with multiple diverse electronic health control devices 56a–56n via a communications medium. Moreover, computer system 10 may communicate with other data processing systems (not shown) via a communications medium.

The communications medium may include wired or wireless communications or other communications media that enables transmission of data to and from computer system 10 and health measurement devices 60a–60n. In a wired embodiment of the present invention, for example, electronic health measurement devices 60a–60n are connected to computer system 10 via parallel, serial, or USB ports, or the communication adapter as depicted in FIG. 1. In a wireless embodiment of the present invention, for example, electronic health measurement devices 60a–60n are connected to computer system 10 via infrared, radio frequency (RF), cellular and other wireless transmissions which are detected by computer system 10.

Data exchange across the communications medium is advantageously performed in at least one of multiple available data transmission protocols and is preferably supported by a common data structure format, such as the extensible mark-up language (XML) data format. Data transmission protocols may include, but are not limited to, Transmission Control Protocol (TCP), Internet Protocol (IP), Hypertext Transfer Protocol (HTTP), and Bluetooth. In addition, data may be transmitted in a secure manner via encryption or by technologies, such as secure socket layer (SSL) or virtual private networks (VPN).

An example of an XML data file that might be transmitted from electonic health measurement devices 60a–60n to portable computer system 10, as depicted below, preferably contains data that is distinguished by attributes on elements and may be wrappered within a larger element. For example, the data attributed to element "<TimeStamp></TimeStamp>" designates the time that the data was attributed to the XML data file.

<PULSE TimeStamp="888965153" TimeRange=
       "888965153,888965185" MachineType="Pulse345"
       Rate="80">

In addition, in an alternate example, the XML data file might be formatted utilizing elements, as illustrated below.

<TimeStamp>888965153</TimeStamp>
    <TimeRange>888965153,888965185</TimeRange>
    <MachineType>Pulse345</MachineType>
    <Rate>80</Rate>

In the example, as will be further described, computer system 10 would receive the example XML data file and utilize the XML data file to compare with a suitable pulse level for a user. The above described XML data file example is intended as a functional example of an XML data file that would detail the pulse rate of an individual. The elements, format of the elements and data included with the elements is provided to depict an example and is not intended to limit the types of elements, format of elements or data included with elements that are in an XML data file.

In the example of the XML data format as the common transmittable data format, a data validation file such as a document type definition (DTD) or schema is preferably utilized to validate XML data files. In addition, a schema preferably translates multiple XML data files. Moreover, a style sheet such as an extensible stylesheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source. In the present example, the DTD or schema would verify that all the data required for reading a pulse is included in the XML data file.

Health measurement devices 60a–60n preferably include multiple diverse health measurement devices, such as a pulse monitor, a blood pressure monitor, an electronic secretion monitor, a perspiration monitor, an electronic scale, an electronic body fat monitor, a stress monitor, a carpal movement monitor, a distance monitor, a respiration monitor, a glucometer, and any other monitoring device that monitors at least one aspect of a user's health or well being. Each of health measurement devices 60a–60n preferably includes a physical health indicator calculator 62a–62n. Physical health indicator calculators 62a–62n preferably compute a numerical physical health indicator of physical health data measured by health measurement devices 60a–60n for a user. In particular, in computing numerical physical health indicators, the computed numbers are preferably associated with a scale of measurement that has been assigned to that type of physical health measurement. Physical health indicators computed by physical health indicator calculators 62a–62n are preferably converted into a common transmittable data format by transmittable format converters 61a–61n, such as XML, and transmitted via the communications medium to computer system 10.

Computer system 10 preferably accesses a data storage medium 40 that includes, but is not limited to including, a health indicator analyzer 42, a health indicator storage 44, a health indicator reference 46, health profile 48, and measurement scheduler 50. In the present embodiment, data storage medium 40 is accessible locally to computer system 10, however in alternate embodiments data storage medium 40 may be externally or remotely accessible to computer system 10, such as via a network connection.

Physical health indicators transmitted from health measurement devices 60a–60n to computer system 10 are preferably stored in health indicator storage 44. Health indicator storage 44 preferably utilizes a data storage structure for storing physical health indicators according to, for example, date and time taken and the type of health measurement device received. Each physical health indicator received at computer system is preferably analyzed by health indicator analyzer 42 to provide the user with an analysis of the most recently received health indicator. In addition, health indicator analyzer 42 is preferably enabled to perform variety of analysis including, but not limited to, a comprehensive overview of physical health according to all the physical health indicators received, an overview of physical health according to physical health indicators received over a particular period of time, and an overview of physical health according to the health measurement device utilized.

Health indicator analyzer 42 is preferably enabled to analyze the physical health indicators stored for a user in health indicator storage 44 over a period of time in order to determine normal levels for a user when sleeping, eating, exercising and working. For example, if when eating over a span of ten days a user's heart rate is detected between 65 and 75 beats per minute, health indicator analyzer 42 may determine that a normal heart rate for the user when eating is between 65 and 75 beats per minute. Moreover, health indicator analyzer 42 is preferably enabled to analyze the physical health indicators over a period of time in order to determine moods associated with levels of physical health. For example, a mood of happiness may be associated with a particular pulse rate while a mood of anxiety may be associated with a particular level of perspiration for a particular user.

In addition to receiving physical health indicators from health measurement devices 60a–60n, a user may input physical health indicators into computer system 10 via an input interface 52 including, but not limited to, a keyboard, a mouse, a stylus, and a vocal recognition system. For example, a user may take their pulse and enter the pulse rate into computer system 10 via input interface 52 rather than utilizing a health measurement device that computes a pulse rate. In addition, a user may input physical health indicators into computer system 10 via input interface 52 that are computed by a health measurement device that is not enabled to transmit physical health indicators.

Health profile 48 includes other health related and non-health related data input to computer system 10 by a user. For example, the user's birthdate, height, physical disabilities, injuries, doctors' information, and other relevant data may be provided. In addition, normal levels for multiple types of physical health indicators may be included. Moreover, health profile 48 may include multiple types of security methods and filters designating multiple levels of security for data stored on computer system 10. For example, the user may indicate that certain parts of health profile 48, such as the user's physical disabilities, are to be shielded from transmittal and access unless a password is supplied. Health indicator analyzer 42 may utilize data such as age, in analyzing physical health indicators. In addition, in analyzing physical health indicators, health indicator analyzer 42 may prompt a user to enter data into health profile 48 that is relevant for the analysis.

Health indicator reference 46 preferably includes reference data for each of the types of physical health indicators measured by health measurement devices 60a–60n, including recommended levels, instructions for compensating for levels and/or dealing with emergencies, and additional data which can be output to the user as needed. Data within health indicator reference 46 can preferably be accessed by the user according to, for example, the health measurement device or type of physical health indicator. In addition, health indicator analyzer 42 may utilize data provided in health indicator reference 46 in analysis and may include or point to data in health indicator reference 46 in analysis reports provided to the user. Data stored within health indicator reference 46 may be downloaded and updated.

In addition, in analyzing physical health indicators received at computer system 10, other health related data for the user may be utilized by health indicator analyzer 42 in analyzing the physical health indicators such as food, liquid and medication intake by the user over a period of time, fitness activity calculated for the user over a period of time, environmental exposure of the user over a period of time, and additional factors that may influence the health of an individual.

Results of analysis performed by health indicator analyzer 42 is preferably output to the user via output interface 54 according to output preferences set by the user in health profile 48. The user-designated output preferences may designate output to multiple types of peripherals accessible to computer system 10. Examples of peripherals include, but are not limited to a graphical display, an electronic paper, an audio speaker, audio headphones, a tactile detectable device, or a printer. In particular, the user may select and provide the type of output device and may upgrade the type of output device as technology advances. The output preferences may include, but are not limited to specifications such as the size, type and coloring of a font in a graphical display, the type of tactile-detectable output (e.g. Braille), the language or the metric amount displayed.

For a graphical display, the user can preferably select from and switch between multiple types of data presentations. For example, the user may select to view of chart or graph of the analyzed data. Alternatively, the user may select to view a spreadsheet representation of the analysis. As previously described, presentation of the data may include data from health indicator reference 46 or may provide a selectable link to particular data within health indicator reference 46. Additional types of data presentations which are not described here may also be utilized for displaying the analyzed data from health indicator analyzer 42.

In response to analysis performed by health indicator analyzer 42, instructions, recommendations and warnings may be output to the user or a warning signal may be triggered such that the user's condition will be dealt with. For example, if an acceptable heart rate for the user when exercising is determined as 120 beats per minute and the detected heart rate for the user while exercising is 150 beats per minute, a warning is preferably output to the user to reduce his/her level of exercise. In addition, recommendations such as decreasing exercise, increasing water consumption, particular stretches and additional information that would aid the user in lowering his/her heart rate may be provided, as retrieved from health indicator reference database 46.

In another example, computer system 10 for a user in a hospital may have access to a warning light or bell, such that in response to analysis of current physical health indicators for the user and analysis of the current physical health indicators in view of acceptable levels for the patient, a warning light or bell may be activated if the physical health indicators are outside of acceptable levels for the user.

In addition, in response to analysis performed by health indicator analyzer 42, a control signal determined by health controller 51 may be output to health control devices 56a–56n to request adjustment to the user's health as controlled by those devices. Health control devices 56a–56n preferably include multiple diverse health control devices that each control a physical aspect of a user's bodily health. For example, in response to a blood sugar level measurement by a health measurement device, health indicator analyzer 42 may determine that the blood sugar level of the user is too low according to the user's health profile and/or the health indicator reference 46. Health controller 51 would determine a control signal to a health control device that injects glucose into the user or reduces injection of insulin at a controlled rate in order to increase the user's blood sugar levels.

An example of an XML data file for a control signal that might be transmitted from portable computer system 10 to electronic health measurement devices 60a–60n, as depicted below, preferably contains data that is distinguished by elements and may be wrapped within a larger element. In the example, a water infuser for supplying water intravenously may be connected to a network at address "90.87.123.3" and control output of 0.5 Liters/hour, for example.

<TimeStamp>888965153</TimeStamp>
<UserID>rt54r</UserID>
<DeviceType>WaterInfuser</DeviceType>
<DeviceAddress>90.87.123.3</DeviceAddress>
<ControlAmount>0.5</ControlAmount>

Data storage medium 40, accessible to computer system 10, may also include a measurement scheduler 50. The types of health measurements which need to be taken from a user and the time frame in which the measurements need to be taken, as indicated by a user or healthcare professional, is preferably stored in measurement scheduler 50. Scheduling data from a healthcare professional may be downloaded onto computer system 10. For example, a healthcare professional may designate that a user needs to take a blood glucose measurement every eight hours with the first measurement of the day occurring at 8 AM. Measurement scheduler 50 preferably schedules an indicator that a blood glucose level measurement needs to be received at 8 AM, 4 PM and 12 AM and stores the indicators in a data storage structure within data storage medium 40. In addition, the health care professional may indicate the grace period for receiving the blood glucose level measurement for 2 hours. Therefore, receiving measurements between 7–9 AM, 3–5 PM and 11–1 AM is acceptable.

For each scheduled measurement, measurement scheduler 50 preferably provides a reminder or series of reminders to the user. For example, a user may be reminded at 7 AM that a measurement needs to be taken. If a measurement has not been received by 9 AM, the user may be reminded that the grace period for taking a measurement has expired. Measurement scheduler 50 may also provide a schedule to the user of when and what measurements need to be taken each day and indicate to the user when the measurement has been received. In particular, if a measurement is not received at all, or is delayed, a record of the lack of receipt or delay may be added to health indicator storage 44. A healthcare professional may access health indicator storage 44 in order to view the measurements taken for a user and to monitor the timeliness of the user in taking measurements.

Physical health indicators, analysis and other data at computer system 10 is preferably transmittable to alternate data processing systems for multiple purposes. For example, physical health indicators may be transmitted from computer system 10 to a doctor's office, such that a doctor can monitor the health of a patient and/or analyze the physical health indicators. In another example, a user may be required to transmit a particular type of health indicator by a particular time, such as a blood analysis. In yet another example, computer system 10 may broadcast physical health indicators, such that alternate data processing systems that are within a particular proximity of computer system 10 may detect the physical health indicators and utilize the indicators for analysis and control of health control devices.

In an alternate example of the present invention, in addition to receiving physical health indicators as measured by a health measurement device, health indicators, such as a disability status may be included in health indicator storage 44. A doctor may provide a designation to computer system 10 that a user is temporarily physically disabled and therefore should be eligible for particular types of handicap parking and other services. The disability status may be transmitted from computer system 10 to a health control device that controls output of a handicap parking sticker, for example.

Computer system 10 is advantageously a portable computer system, such as a digital telephone, a personal digital assistant, a laptop computer, or a palmtop computer that is easily transportable and compact. In addition, computer system 10 is advantageously utilized as a personal health monitor for monitoring health across multiple diverse health measurement devices and a temporary controller for controlling multiple diverse health control devices. It is important to note that a user is able to customize the features available on computer system 10. Since the user advantageously supplies computer system 10, the user may select the type and quality of desired output. In addition, it is important to note that computer system 10 may be continuously upgraded without requiring the upgrade of exercise machine 38.

In addition, it is important to note that the health measurement monitoring system of the present invention may provide for a setting in which a user's account included in health profile 48 is charged as the user utilizes health measurement devices 60a–60n. For example, a user's account may be debited per measurement device usage, per type of measurement device utilized, per time utilizing the measurement device, or other criteria.

Figure 3:
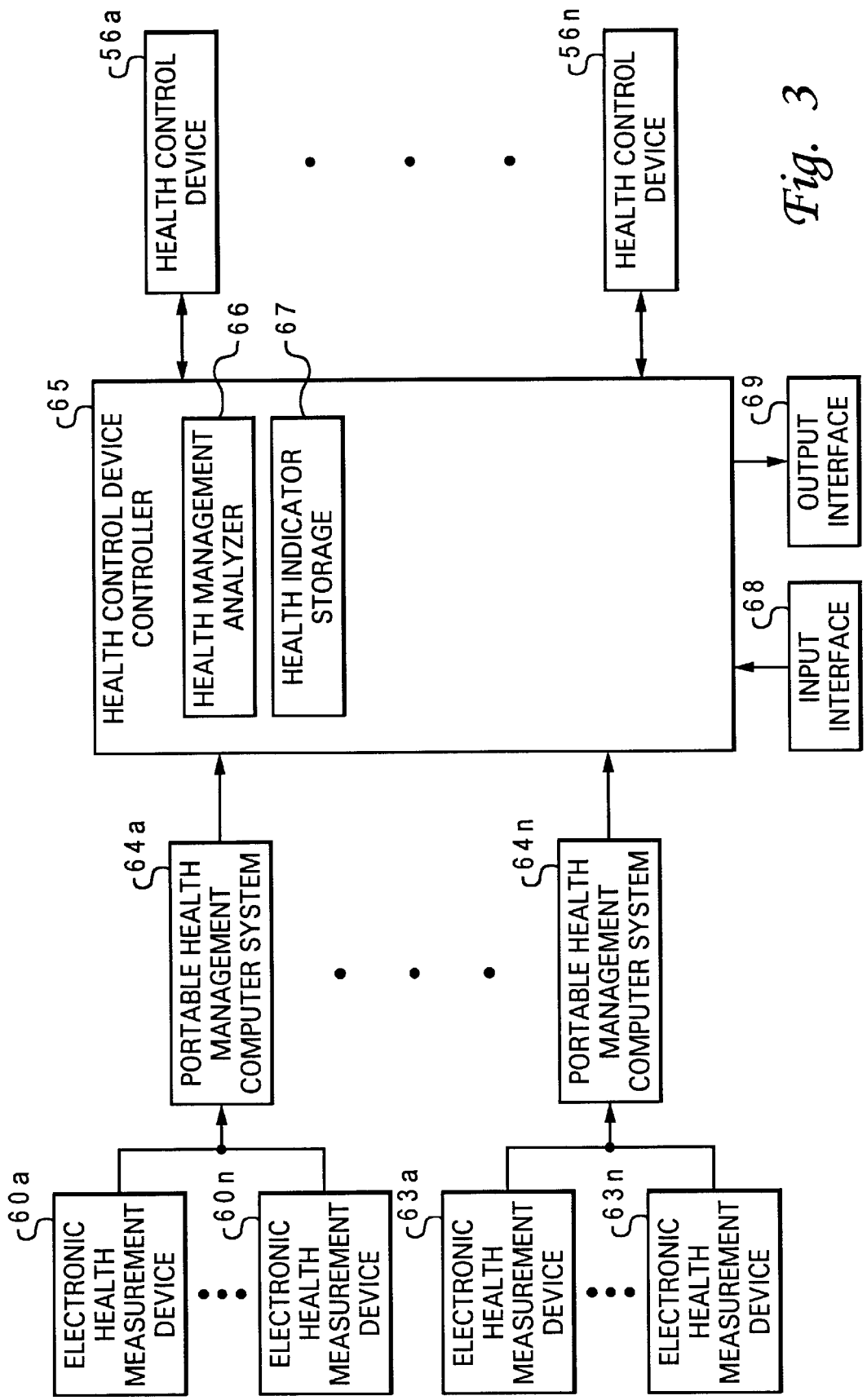
FIG. 3 depicts one embodiment of a block diagram of a health control device controller in accordance with the method, system and program of the present invention.

Referring now to FIG. 3, there is depicted one embodiment of a block diagram of a health control device controller in accordance with the method, system and program of the present invention. As depicted, multiple portable health management computer systems 64a–64n, such as computer system 10, receive physical health indicators respectively from multiple electronic health measurement devices 60a–60n and 63a–63n. Health management computer systems 64a–64n preferably transmit physical health indicators, analysis and control signals to health control device controller 65.

Health control device controller 65 preferably includes a health management analyzer application 66 for analyzing data received at health control device controller 65 and health indicator storage 67 for recording data received at health control device controller 65. In particular, health control device controller 65 may be enabled to control multiple diverse health control devices 56a–56n depending upon physical health indicators received from health management computer systems 64a–64n, from health measurement devices coupled to health control device controller 65, and from health related data input via input interface 68. In addition, health control device controller 65 may be enabled to output recommendations to a user of manager via output interface 69.

Health management analyzer application 66 preferably samples data transmissions indicating health from multiple users via health management computer systems 64a–64n. Health management analyzer application preferably analyzes the sampled data in order to determine health conditions within a sampled group, determine an overall mood of a sampled group, and/or control health control devices 56a–56n within a sampled group. For example, in a stadium, a health control device controller would receive physical health indicator levels from multiple spectators. Health management analyzer 66 may determine whether there are spectators with health conditions that should be monitored and medical assistants alerted. In addition, health management analyzer 66 may determine the general mood of the crowd. If detected pulse rates are on average thirty beats per minute faster than normal, then a mood of excitement may be determined. In addition, current pulse rates may be compared against previous pulse rates to determine what types of events cause different types of crowd moods. Moreover, health management analyzer 66 may determine that a crowd is getting too hot based on levels of perspiration health indicators and activate misters or other health control devices that would cool the spectators.

In another example, a corporation or other group may monitor employee health, employee moods and other data via health control device controller 65. For example, the anxiety level within a meeting room may be detected if perspiration health indicators and pulse indicators are transmitted from health management computer systems 64a–64n for each of the participants. Moreover, health control device controller 65 may be utilized as a lie detector by recording physical health indicator levels for a particular person that indicate lack of truth and in response to receiving similar levels, alerting a supervisor.

In yet another example, multiple users may elect to transmit physical health indicators to a controller that also monitors what the multiple users are watching or hearing, such as television or radio. Health management analyzer 66 would analyze the physical health indicators in view of the monitored intake by the multiple users and determine the types of physical reactions that users experience in response what is heard or seen. For example, a children's television show may elicit increases in heart rates in children watching the program when a particular character is shown. If the goal of the show is to keep children active and excited, that particular character may be shown more often, for example.

Referring now to FIG. 4, there is depicted a block diagram of a data storage structure for the health indicator storage in accordance with the method, system and program of the present invention. As depicted, a data storage structure 70 includes multiple categorized entries. Health indicators and other data from multiple types of health measurement devices may be stored in data storage structure 70 as converted from an XML data file. While one type of data storage structure is depicted, in alternate embodiments, alternate types of data storage structures may be utilized. In addition, the user for which health indicators have been received is preferably designated in data storage structure 80 when there are multiple users A first category indicated at reference numeral 72 includes health indicator measurements. Next, a second category indicated at reference numeral 74 designates the date and time that the indicator measurement was taken. Thereafter, a third category indicated at reference numeral 76 includes the measurement unit. In the example provided, multiple entries are provided in each category as depicted at reference numeral 78. For example, on "11/20/2000" at "06:10:20" a pulse rate measurement taken in beats/minute was recorded with 60 beats/minute.

With reference now to FIG. 5, there is illustrated a block diagram of a data storage structure for the measurement scheduler in accordance with the method, system and program of the present invention. As depicted, a data storage structure 80 includes multiple categorized entries. Measurement scheduling for multiple types of health measurement devices may be stored in data storage structure 80. While one type of data storage structure is illustrated, in alternate embodiments, alternate types of data storage structures may be utilized. In addition, the user for which measurements have been scheduled is preferably designated in data storage structure 80 when there are multiple users.

A first category indicated at reference numeral 82 includes the type of measurement to take. Next, a second category indicated at reference numeral 84 designates the date and time to take the measurement. Thereafter, a third category indicated at reference numeral 86 includes the range of time. In the example provided, multiple entries are provided in each category as depicted at reference numeral 88. For example, blood pressure readings are scheduled to be taken on "11/18/2000" between "9:00:00" and "11:00:00" and between "15:00:00" and "17:00:00". In addition, in the example, a heart rate reading is scheduled to be taken on "11/18/2000" between "10:30:00" and "11:30:00".

Figure 6:
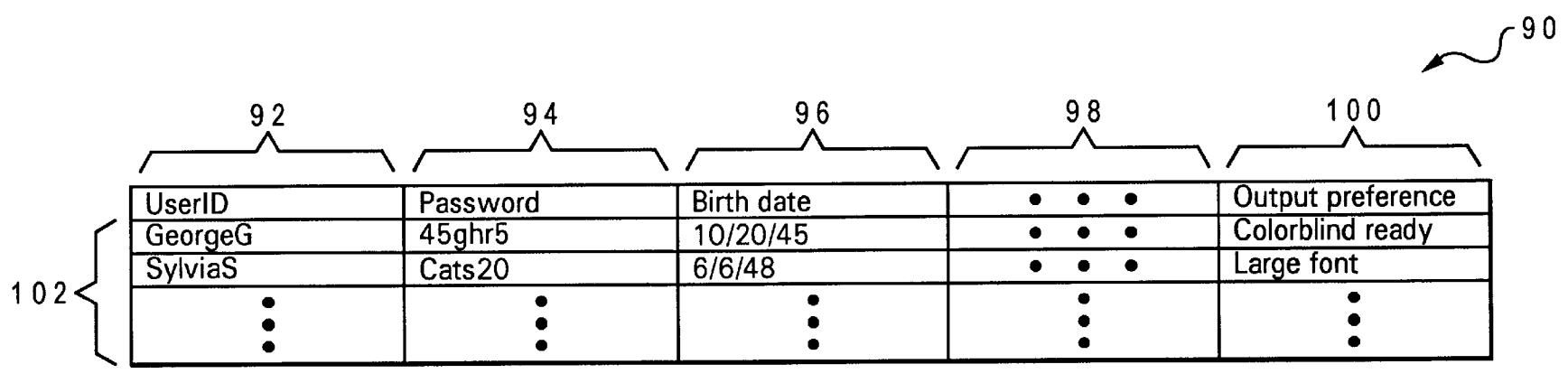

Referring now to FIG. 6, there is depicted a block diagram of a data storage structure for health profiles in accordance with the method, system and program of the present embodiment. As illustrated a data storage structure 90 includes multiple categorized entries. Health profiles for multiple users may be stored in data storage structure 90 as converted from an XML data file. While one type of data storage structure is illustrated, in alternate embodiments, alternate types of data storage structures may be utilized.

A first category indicated at reference numeral 92 includes the userID. Next, a second category indicated at reference numeral 94 designates the password for the userID. Thereafter, a third category indicated at reference numeral 96 includes the birth date. Next, multiple additional categories are indicated at reference numeral 98 with the last category indicated at reference numeral 100 including the output preferences. In the examples provided, multiple entries are provided in each category as depicted at reference numeral 102. For example, a user "GeorgeG" has a password of "45ghr5" and was born on "10/20/45". Additional data about "GeorgeG" is preferably included under additional categories indicated at reference numeral 98. In addition, the output preference for "GeorgeG" indicates that any output should be colorblind ready. Thus data output for "GeorgeG" will not utilize colors that are not detectable by a colorblind user.

Figure 7:
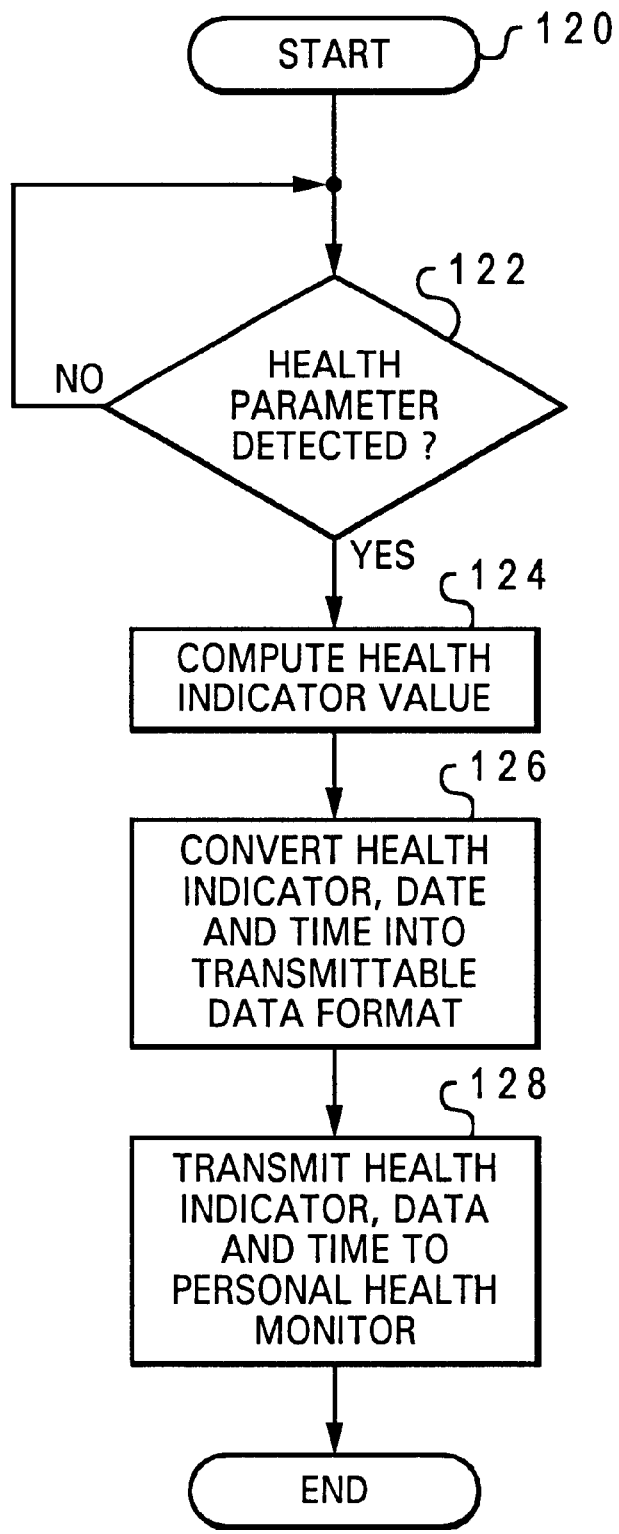
FIG. 7 illustrates a high level logic flowchart of a process and program for transmitting health indicators to a personal health indicator monitoring system in accordance with the method, system and program of the present invention.

With reference now to FIG. 7, there is illustrated a high level logic flowchart of a process and program for transmitting health indicators to a personal health indicator monitoring system in accordance with the method, system and program of the present invention. As depicted, the process starts at block 120 and thereafter proceeds to block 122. Block 122 illustrates a determination as to whether or not a health parameter is detected. Each health measurement device will detect different types of health parameters. For example, a pulse measurement device will detect a pulse rate for a user. If a health parameter is not detected, the process iterates at block 122. If a health parameter is detected, the process passes to block 124. Block 124 depicts computing a health indicator value. In the example of the pulse measurement device, a health indicator value of beats/minute is preferably computed. Thereafter, block 126 illustrates converting the health indicator and date and time of receipt into a common transmittable data format. Next, block 128 depicts transmitting the health indicator and data and time of receipt to a personal health monitor and the process ends.

Figure 8:
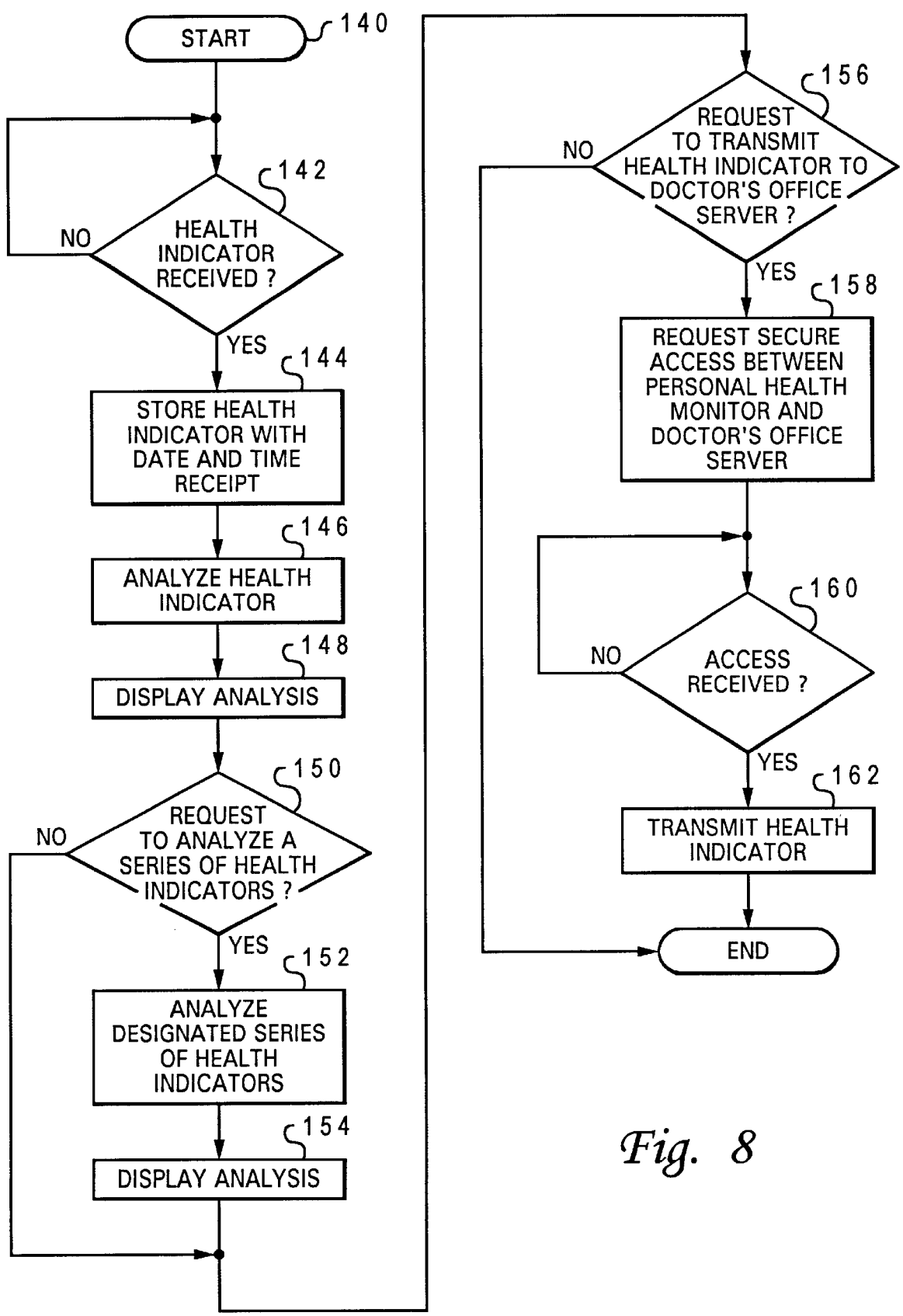
FIG. 8 depicts a high level logic flowchart of a process and program for processing health indicators received at a personal health monitor in accordance with the method, system and program of the present invention.

Referring now to FIG. 8, there is depicted a high level logic flowchart of a process and program for processing health indicators received at a personal health monitor in accordance with the method, system and program of the present invention. As illustrated, the process starts at block 140 and thereafter proceeds to block 142. Block 142 depicts a determination as to whether or not a health indicator is received. If a health indicator is received, the process passes to block 144. Block 144 illustrates storing the health indicator with data and time receipt. Thereafter, block 146 depicts analyzing the received health indicator. Next, block 148 illustrates displaying results from the analysis. In particular, the analysis may also be output to other output devices. In addition, the analysis is preferably displayed according to any user output preferences stored in the health profile. Thereafter, block 150 depicts a determination as to whether or not a request to analyze a series of health indicators. In particular a request may be made to analyze a series of health indicators according to a time period, date, indicator type, etc as designated by the user. If a request to analyze a series of health indicators is not made, the process passes to block 156. If a request to analyze a series of health indicators is made, the process passes to block 152. Block 152 illustrates analyzing the designated series of health indicators. Thereafter, block 154 depicts displaying the results from the analysis and the process passes to block 156.

Block 156 depicts a determination as to whether or not a request to transmit a health indicator(s) to a doctor's office server is made. In particular, a doctor's office server may represent a health care provider of any type. If a request to transmit a health indicator is not made, the process ends. If a request to transmit a health indicator is made, the process passes to block 158. Block 158 illustrates requesting secure access between the personal health monitor and the doctor's office server. Next, block 160 depicts a determination as to whether or not secure access is received. If secure access is not received, the process iterates at block 160. If secure access is received, the process passes to block 162. Block 162 illustrates transmitting the health indicator(s) and the process ends.

Figure 9:
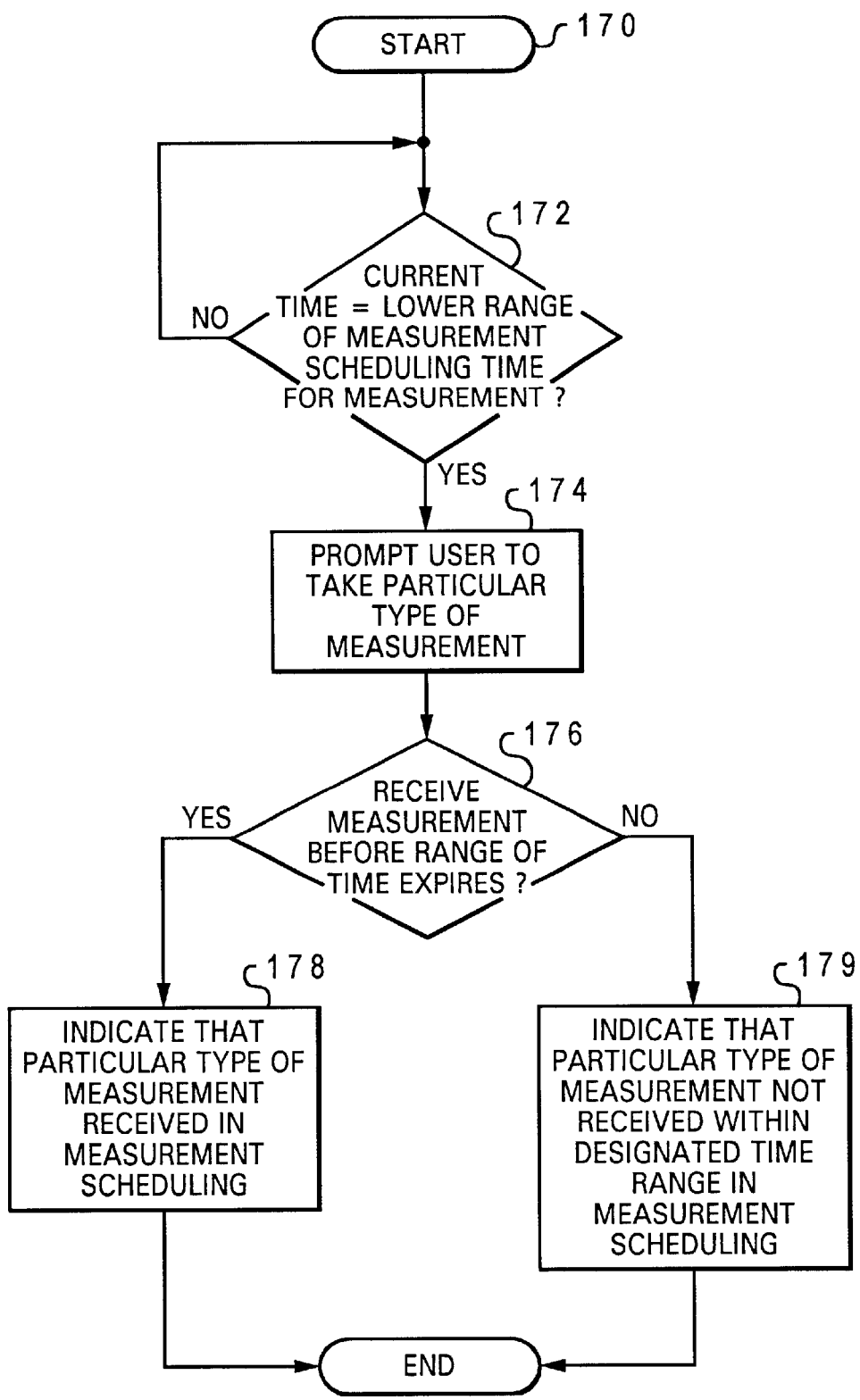
FIG. 9 illustrates a high level logic flowchart of a process and program for monitoring receipt of health indicators in accordance with the method, system and program of the present invention.

With reference now to FIG. 9, there is illustrated a high level logic flowchart of a process and program for monitoring receipt of health indicators in accordance with the method, system and program of the present invention. As depicted, the process starts at block 170 and thereafter proceeds to block 172. Block 172 illustrates a determination as to whether or not the current time is equal to the lower range of a measurement scheduling time. If the current time is not equal to the lower range of a measurement scheduling time, the process iterates at block 172. If the current time is equal to the lower range of a measurement scheduling time, the process passes to block 174. Block 174 depicts prompting the user to take a particular type of measurement according to the measurement type scheduled for the measurement scheduling time. Thereafter, block 176 illustrates a determination as to whether or not the health indicator measurement is received before the range of time scheduled for the measurement expires. If the measurement is received before the range of time expires, the process passes to block 178. Block 178 depicts indicating that the particular type of measurement is received in the measurement scheduling record and the process ends. If the measurement is not received before the range of time scheduled for the measurement expires, the process passes to block 180. Block 180 illustrates indicating that the particular type of measurement was not received within the designated range of time in the measurement scheduling record and the process ends.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A method for monitoring acceptability of the physical health of an individual, said method comprising the steps of:

receiving a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

analyzing each of said plurality of physical health indicators at said portable computer system in view of determined acceptable health levels for said particular user;

controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices; and controlling output of recommended actions for said particular user, in response to results from said analysis indicating that said plurality of physical health indicators are outside of a normal range of physical health for said particular user.

2. A method for monitoring acceptability of the physical health of an individual, said method comprising the steps of:

receiving a plurality of physical health indicators in an extensible mark-up data format computed for a particular user in a common transmittable data format at a portable computer system associated with said particular user, wherein each of said plurality of physical health indicators is computed by an electronic health measurement device from among a plurality of diverse electronic health measurement devices monitoring said particular user;

analyzing each of said plurality of physical health indicators at said portable computer system in view of determined acceptable health levels for said particular user;

controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices.

3. The method for monitoring acceptability of the physical health of an individual according to claim 1, said step of controlling output of an indicator of acceptability further comprising the step of:

controlling output of said indicator of acceptability to an output interface controlled by said portable computer system.

4. The method for monitoring acceptability of the physical health of an individual according to claim 1, said step of controlling output of an indicator of acceptability further comprising the step of:

controlling transmission of said indicator of acceptability from said portable computer system to a warning device.

5. The method for monitoring acceptability of the physical health of an individual according to claim 1, said step of controlling output of an indicator of acceptability further comprising the step of:

controlling output of an indicator that said plurality of physical health indicators are within a normal range of physical health for said particular user.

6. The method for monitoring acceptability of the physical health of an individual according to claim 1, said method further comprising the step of:

controlling transmission of a plurality of control signals to a plurality of health control devices that control said physical health of said particular user according to said plurality of control signals from said portable computer system.

7. A method for monitoring acceptability of the physical health of an individual, said method comprising the steps of:

receiving a plurality of physical health indicators in an extensible mark-up data format computed for a particular user in a common transmittable data format at a portable computer system associated with said particular user, wherein each of said plurality of physical health indicators is computed by an electronic health measurement device from among a plurality of diverse electronic health measurement devices monitoring said particular user;

analyzing each of said plurality of physical health indicators at said portable computer system in view of normal health levels for said particular user determined by said portable computer system from monitoring said plurality of physical health indicators for said particular user over a particular period of time;

controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices; and controlling output of an indicator of acceptability, wherein controlling output of recommended actions for said particular user, in response to results from said analysis indicating that said plurality of physical health indicators are outside of a normal range of physical health for said particular user.

8. The method for monitoring acceptability of the physical health of an individual according to claim 1, said step of analyzing each of said plurality of physical health indicators at said portable computer system in view of determined acceptable health levels for said particular user further comprising the step of:

analyzing each of said plurality of physical health indicators at said portable computer system in view of normal health levels cited in a health indicator reference database stored at said portable computer system.

9. A method for monitoring acceptability of the physical health of an individual, said method comprising the steps of:

receiving a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

analyzing each of said plurality of physical health indicators at said portable computer system in view of determined acceptable health levels for said particular user;

controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices;

designating a time period during which a particular physical health indicator is expected to be received at said portable computer system; and prompting said user to utilize an electronic health measurement device to determine said particular physical health indicator during said designated time period.

10. A system for monitoring acceptability of the physical health of an individual, said system comprising:

means for receiving a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of determined acceptable health levels for said particular user;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices; and controlling output of an indicator of acceptability, wherein means for controlling output of recommended actions for said particular user, in response to results from said analysis indicating that said plurality of physical health indicators are outside of a normal range of physical health for said particular user.

11. A system for monitoring acceptability of the physical health of an individual, said system comprising:

means for receiving a plurality of physical health indicators computed for a particular user in an extensible mark-up language data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of determined acceptable health levels for said particular user;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices; and controlling output of an indicator of acceptability, wherein means for controlling output of recommended actions for said particular user, in response to results from said analysis indicating that said plurality of physical health indicators are outside of a normal range of physical health for said particular user.

12. The system for monitoring acceptability of the physical health of an individual according to claim 10, said means for controlling output of an indicator of acceptability further comprising:

means for controlling output of said indicator of acceptability to an output interface controlled by said portable computer system.

13. The system for monitoring acceptability of the physical health of an individual according to claim 10, said means for controlling output of an indicator of acceptability further comprising:

means for controlling transmission of said indicator of acceptability from said portable computer system to a warning device.

14. The system for monitoring acceptability of the physical health of an individual according to claim 10, said means for controlling output of an indicator of acceptability further comprising:

means for controlling output of an indicator that said plurality of physical health indicators are within a normal range of physical health for said particular user.

15. The system for monitoring acceptability of the physical health of an individual according to claim 10, said system further comprising:

means for controlling transmission of a plurality of control signals to a plurality of health control devices that control said physical health of said particular user according to said plurality of control signals from said portable computer system.

16. A system for monitoring acceptability of the physical health of an individual, said system comprising:

means for receiving a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of normal health levels for said particular user determined by said portable computer system from monitoring said plurality of physical health indicators for said particular user over a particular period of time;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices; and controlling output of an indicator of acceptability, wherein means for controlling output of recommended actions for said particular user, in response to results from said analysis indicating that said plurality of physical health indicators are outside of a normal range of physical health for said particular user.

17. The system for monitoring acceptability of the physical health of an individual according to claim 10, said means for analyzing each of said plurality of physical health indicators at said portable computer system in view of determined acceptable health levels for said particular user further comprising:

means for analyzing each of said plurality of physical health indicators at said portable computer system in view of normal health levels cited in a health indicator reference database stored at said portable computer system.

18. A system for monitoring acceptability of the physical health of an individual, said system comprising:

means for receiving a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of determined acceptable health levels for said particular user;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices;

controlling output of an indicator of acceptability, wherein means for controlling output of recommended actions for said particular user, in response to results from said analysis indicating that said plurality of physical health indicators are outside of a normal range of physical health for said particular user;

means for designating a time period during which a particular physical health indicator is expected to be received at said portable computer system; and means for prompting said user to utilize an electronic health measurement device to determine said particular physical health indicator during said designated time period.

19. A program for monitoring acceptability of the physical health of an individual, residing on a computer readable medium having computer readable program code means, said program comprising:

means for enabling reception of a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of determined acceptable health levels for said particular user;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices; and means for controlling output of recommended actions for said particular user, in response to results from said analysis indicating that said plurality of physical health indicators are outside of a normal range of physical health for said particular user.

20. A program for monitoring acceptability of the physical health of an individual, residing on a computer readable medium having computer readable program code means, said program comprising:

means for enabling reception of a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of determined acceptable health levels for said particular user;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices;

program for monitoring acceptability of the physical health of an individual, wherein means for controlling output of recommended actions for said particular user, in response to results from said analysis indicating that said plurality of physical health indicators are outside of a normal range of physical health for said particular user; and means for enabling reception of said plurality of physical health indicators in an extensible mark-up language data format.

21. The program for monitoring acceptability of the physical health of an individual according to claim 19, said program further comprising:

means for controlling output of said indicator of acceptability to an output interface controlled by said portable computer system.

22. The program for monitoring acceptability of the physical health of an individual according to claim 19, said program further comprising:

means for controlling transmission of said indicator of acceptability from said portable computer system to a warning device.

23. The program for monitoring acceptability of the physical health of an individual according to claim 19, said program further comprising:

means for controlling output of an indicator that said plurality of physical health indicators are within a formal range of physical health for said particular user.

24. The program for monitoring acceptability of the physical health of an individual according to claim 19, said program further comprising:

means for controlling transmission of a plurality of control signals to a plurality of health control devices that control said physical health of said particular user according to said plurality of control signals from said portable computer system.

25. A program for monitoring acceptability of the physical health of an individual, residing on a computer readable medium having computer readable program code means, said program comprising:

means for enabling reception of a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of determined acceptable health levels for said particular user;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices; and means for analyzing each of said plurality of physical health indicators at said portable computer system in view of normal health levels for said particular user determined by said portable computer system from monitoring said plurality of physical health indicators for said particular user over a particular period of time.

26. The program for monitoring acceptability of the physical health of an individual according to claim 19, said program further comprising:

means for analyzing each of said plurality of physical health indicators at said portable computer system in view of normal health levels cited in a health indicator reference database stored at said portable computer system.

27. A program for monitoring acceptability of the physical health of an individual, residing on a computer readable medium having computer readable program code means, said program comprising:

means for enabling reception of a plurality of physical health indicators computed for a particular user in a common transmittable data format at a portable computer system associated with said particular user, wherein each of said plurality of physical health indicators is computed by an electronic health measurement device from among a plurality of diverse electronic health measurement devices monitoring said particular user;

means for analyzing each of said plurality of physical health indicators at said portable computer system in view of determined acceptable health levels for said particular user;

means for controlling output of an indicator of acceptability of said plurality of physical health indicators for said particular user from said portable computer system, in response to said analysis of each of said plurality of physical health indicators, such that a single portable computer system monitors the physical health of an individual from a plurality of physical health indicators received from a plurality of diverse electronic health measurement devices;

means for designating a time period during which a particular physical health indicator is expected to be received at said portable computer system; and prompting said user to utilize an electronic health measurement device to determine said particular physical health indicator during said designated time period.

28. A method for managing the physical health of a plurality of users, said method comprising the steps of:

receiving a plurality of physical health indicators for a plurality of users from a plurality of portable computer systems each respectively provided by one of said plurality of users;

analyzing said plurality of physical health indicators in view of a common setting in which said plurality of users are located; and determining an average health profile of said plurality of users, in response to said analyzing of said plurality of physical health indicators in view of a common setting in which said plurality of users are located.

29. The method for managing the physical health of a plurality of users according to claim 28, said method further comprising the step of:

controlling output of a plurality of control signals each respectively to one of a plurality of health control devices that each control a particular parameter of said physical health of said plurality of users.

30. The method for managing the physical health of a plurality of users according to claim 28, said method further comprising the step of:

determining average physical responses from said plurality of users to a plurality of events within said common setting over a particular period of time.

31. A system for managing the physical health of a plurality of users, said system comprising:

means for receiving a plurality of physical health indicators for a plurality of users from a plurality of portable computer systems each respectively provided by one of said plurality of users;

means for analyzing said plurality of physical health indicators in view of a common location in which said plurality of users are situated; and means for determining an average health profile of said plurality of users, in response to said analyzing of said plurality of physical health indicators in view of a common location in which said plurality of users are situated.

32. The system for managing the physical health of a plurality of users according to claim 31, said system further comprising:

means for controlling output of a plurality of control signals each respectively to one of a plurality of health control devices that each control a particular parameter of said physical health of said plurality of users.

33. The system for managing the physical health of a plurality of users according to claim 31, said system further comprising the step of:

means for determining average physical responses from said plurality of users to a plurality of events within said common location over a particular period of time.

* * * * *